Figure 2:
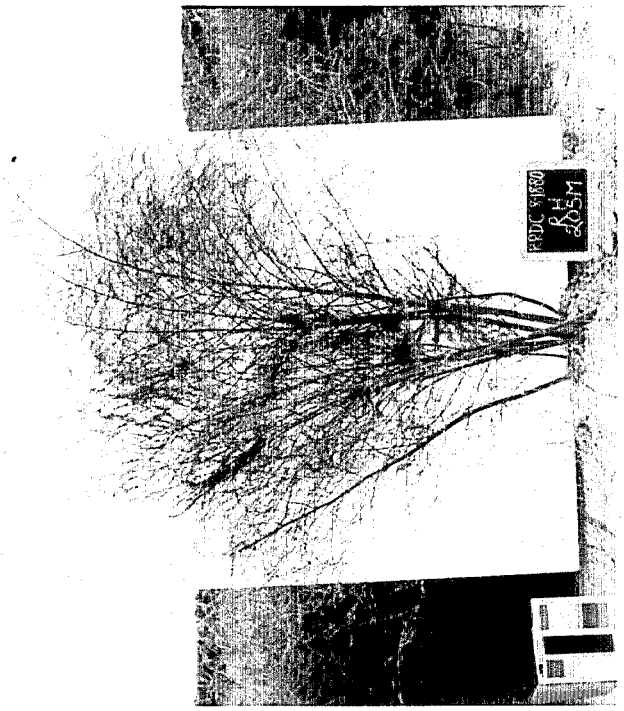

United States Patent [19]

Ellison et al.

[11] Patent Number: Plant 5,551

[45] Date of Patent: Sep. 3, 1985

[54] ASPARAGUS PLANT-JERSEY GIANT

[75] Inventors: J. Howard Ellison, Milltown; John J. Kinelski, Princeton, both of N.J.

[73] Assignee: Rutgers University, New Brunswick, N.J.

[21] Appl. No.: 544,109

[22] Filed: Oct. 21, 1983

[51] Int. Cl.[3] ..... A01H 5/00

[52] U.S. Cl. ..... Plt./89

[58] Field of Search ..... Plt./89

*Primary Examiner*—Robert E. Bagwill

*Attorney, Agent, or Firm*—Frank B. Robb

[57] ABSTRACT

An all male asparagus hybrid resulting from a cross of female asparagus plant No. 56 (unpatented) and male plant No. 22-8 (unpatented) having high yield ability, resistance to rust (*Puccinia asparagi*) good field tolerance to root and crown rot (*Fusarium oxysporum* and *F. moniliforme*) together with excellent geographic adaptability.

2 Drawing Figures

This invention relates to a new variety of Asparagus Plant, which is one of many plants developed by us in a broad program of asparagus improvement having several objectives, including improved resistance or desirably complete resistance to diseases such as rust (*Puccinia asparagi*) as well as good tolerance to root and crown rot (*Fusarium oxysporum* and *F. moniliforme*).

Probably the most important objective in any such program however is to produce plants which have increased yield as well as larger and longer spears and which in turn appeal to the market.

The instant variety which we have chosen to denominate as "Jersey Giant", originally identified by us as No. 56×22-8, is one which has all of the foregoing attributes and as compared to some of the standard varieties such as Mary Washington (an unpatented variety) well known as an industry standard, the same is clearly superior.

The instant variety "Jersey Giant" was originated by crossing the seed patent "Donna" (an unpatented variety) with the pollen parent "Scott Howard" (also an unpatented variety), both of the foregoing having been developed by us, and as will be understood embodying the best characteristics of each.

In fact comparison in early yield (two weeks) and in fusarium infested soil in the vicinity of Bridgeton, N.J., the production of jumbo spears (larger than 10/16" diameter, 9" long) has shown that "Jersey Giant" our new variety has produced on the order of four times the number and about three times the total marketable spears 6/16" and larger diameter, 9" long.

When our new variety is grown in New Jersey, in fusarium infested fields it also produced about double the weight of marketable spears as compared with other varieties, some selections of Mary Washington and also unpatented, such as "Rutgers Beacon".

Of interest and indicative of the effect of fusarium infestation, is the fact that even in soils virgin to asparagus, our new variety still out produces, producing marketable yields usually twice that of Mary Washington in any event.

A compilation of data, setting forth actual results of growing our new variety in substantially different geographical locations, and in soil virgin to asparagus as well, follows hereafter and indicates the superiority we have developed in "Jersey Giant".

ASPARAGUS PLANT NO. 56×22-8 MALE HYBRID - "JERSEY GIANT"

TABLE 1

Bridgeton, New Jersey Early Yield (Two weeks). Fusarium infested soil.

| | Jumbo[1] | | | Total Marketable[2] | | |
|---|---|---|---|---|---|---|
| | 1981 | 1982 | Mean | 1981 | 1982 | Mean |
| 56 X 22-8 | 462[4] | 957 | 710 | 1185 | 1678 | 1432 |
| Mary Washington | 137 | 199 | 168 | 494 | 809 | 652 |

TABLE 2

Mickleton, New Jersey Early yield (2 weeks). Fusarium infested soil. 1982.

| | Jumbo[1] | Total Marketable[2] |
|---|---|---|
| 56 X 22-8 | 494[4] | 1316 |
| Rutgers Beacon | 223 | 639 |

TABLE 3

Woodstown, New Jersey (2 weeks). Soil virgin to asparagus.

| | Jumbo Spears[1] | | | | Total Marketable Spears[2] | | | |
|---|---|---|---|---|---|---|---|---|
| | 1980 | 1981 | 1982 | Mean | 1980 | 1981 | 1982 | Mean |
| 56 X 22-8 | 388 | 460 | 984 | 611 | 760 | 930 | 1582 | 1091 |
| Rutgers Beacon | 325 | 322 | 516 | 388 | 612 | 766 | 1110 | 829 |

TABLE 4

Bixby, Oklahoma. Marketable yield snapped spears 9" and shorter, 6/16" diameter and larger. Soil virgin to asparagus.

| | 1979 | 1980 | 1981 | Mean |
|---|---|---|---|---|
| 56 X 22-8 | 797[4] | 2554 | 5024 | 2792 |
| Mary Washington | 393 | 818 | 2633 | 1281 |

TABLE 5

Michigan. Soil virgin to asparagus.

| | Sodus Marketable Yield[2] | | | Oceana County Marketable Yield[2] | | |
|---|---|---|---|---|---|---|
| | 1981 | 1982 | Mean | 1981 | 1982 | Mean |
| 56 X 22-8 | 296[4] | 396 | 346 | 389 | 1501 | 945 |
| Mary Washington | 99 | 100 | 100 | 120 | 601 | 360 |

TABLE 6

| Clinton, North Carolina. Soil virgin to asparagus. | Marketable Spears[2] (two weeks) | | | |
|---|---|---|---|---|
| | 1980 | 1981 | 1982 | Mean |
| 56 X 22-8 | 1086[4] | 2202 | 1707 | 1665 |
| Robert Super[3] | 253 | 721 | 694 | 556 |

TABLE 7

| Guelph, Ontario, Canada. Soil virgin to asparagus. | Marketable Spears[2] (two weeks) 1982 |
|---|---|
| 56 X 22-8 | 1384[4] |
| Mary Washington | 870 |

Figure 1:
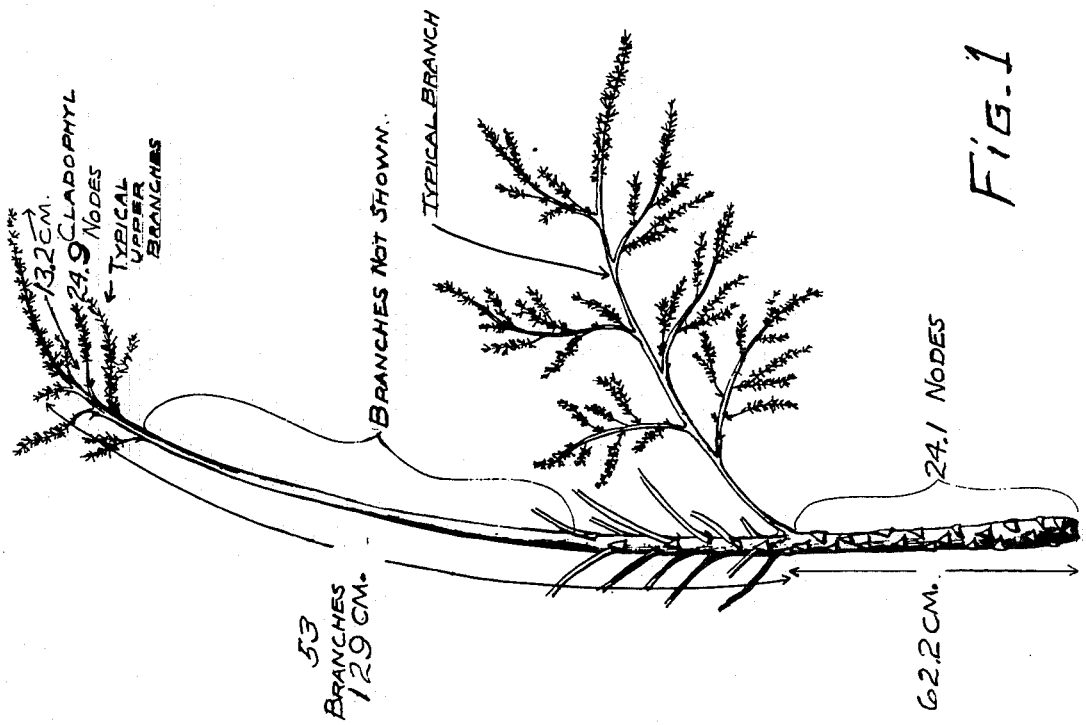

[1]Spears larger than 10/16" diameter, 9" long
[2]Spears 6/16" and larger diameter, 9" long
[3]Selection of Mary Washington
[4]All data are pounds per acre In the drawing attached hereto we have also supplied data which indicated thereon in reference to a stalk of a typical plant shown in black and white, in FIG. 1, and in FIG. 2 a typical plant in color as nearly representative as it is possible to make the same in an illustration of this kind, some of the details being obviously obscured and the color affected by density and light, though the illustration was made as a result of normal field conditions on a day of average sunlight.

ASPARAGUS PLANT NO. 56×22-8 MALE HYBRID "JERSEY GIANT"

| Stalk Data | |
|---|---|
| Number of nodes below first branch | 24.1 |
| Number of cm from crown to first branch | 62.2 |
| Number of branches | 53 |
| Number cm between first and last branch | 129 |
| Internode length in cm between branches | 2.44 |

-continued

| | |
|---|---|
| Number of cladophyll nodes beyond last branch | 24.9 |
| Number of cm beyond last branch | 13.2 |
| Internode length in cm beyond last branch | 0.53 |
| Largest stalk diameter in mm | 17.6 |
| Mature stalk color, bloom removed | 22–13 |
| Flower Data | |
| Petal tip (yellow) | 24–5 |
| Petal base (brown) | 29–13 |
| Flower length in mm | 6.74 |
| Flower width at midpoint in mm | 2.92 |

[(1)]Color number, Munsell Limit Color Cascade, Munsell Color, Macbeth Color and Photometry Division, 2441 Calvert Street, Baltimore, Maryland 21218

We have caused our new variety "Jersey Giant" to be asexually reproduced in the vicinity of New Brunswick, N.J. and find that it does come true in successive generations.

Our new variety was asexually reproduced by crown division.

We also note that the female parent, No. 56, not being patented, is currently the subject matter of patent application as well as the variety No. 22-8 the male parent likewise.

We note that as is well known also the male plant is capable of greater yield for a longer period of time than the female plant and thus any male characteristics which are carried in the hybrid which we have set forth is described herein, will be of benefit and provide advantage in the market place.

We claim:

1. A new and distinct variety of Asparagus Plant as herein shown and described, characterized as to novelty by the unique combination as an all male hybrid, of high yield ability, resistance to rust (*Puccinia asparagi*) and good field tolerance to root and crown rot (*Fusarium oxysporum* and *F. moniliforme*), with outstanding geographic adaptation, yielding well under widely varying conditions.

* * * * *